(12) United States Patent
Lee et al.

(10) Patent No.: US 11,366,058 B2
(45) Date of Patent: Jun. 21, 2022

(54) OUTDOOR MULTI-PASS CELL FOR TDLAS

(71) Applicant: KOREA INSTITUTE OF INDUSTRIAL TECHNOLOGY, Cheonan-si (KR)

(72) Inventors: Chang Yeop Lee, Seoul (KR); Mi Yeon Yoo, Pyeongtaek-si (KR); Sung Hyun So, Changwon-si (KR); Sae Rom Maeng, Cheongju-si (KR)

(73) Assignee: KOREA INSTITUTE OF INDUSTRIAL TECHNOLOGY, Cheonan-Si (KR)

( * ) Notice: Subject to any disclaimer, the term of this patent is extended or adjusted under 35 U.S.C. 154(b) by 0 days.

(21) Appl. No.: 16/758,856

(22) PCT Filed: Oct. 5, 2018

(86) PCT No.: PCT/KR2018/011802
§ 371 (c)(1),
(2) Date: Apr. 24, 2020

(87) PCT Pub. No.: WO2019/088479
PCT Pub. Date: May 9, 2019

(65) Prior Publication Data
US 2021/0199572 A1    Jul. 1, 2021

(30) Foreign Application Priority Data

Oct. 31, 2017  (KR) .................. 10-2017-0144030
Oct. 31, 2017  (KR) .................. 10-2017-0144044

(51) Int. Cl.
*G01N 21/39*    (2006.01)
*G01N 21/03*    (2006.01)
(Continued)

(52) U.S. Cl.
CPC .......... *G01N 21/39* (2013.01); *G01N 21/031* (2013.01); *G01N 21/0332* (2013.01);
(Continued)

(58) Field of Classification Search
CPC .............. G01N 21/39; G01N 21/0332; G01N 21/3504; G01N 33/0037; G01N 33/0042;
(Continued)

(56) References Cited

U.S. PATENT DOCUMENTS 6,298,669 B1    10/2001  Maruyama et al.
6,486,474 B1 *  11/2002  Owen .................. G01N 21/031
                                                      250/339.02
(Continued)

FOREIGN PATENT DOCUMENTS

JP       571751 U       9/1993
JP       2001133105 A   5/2001
(Continued)

OTHER PUBLICATIONS

Bela Tuzson et al., "Compact multipass optical cell for laser spectroscopy," Optics Letters, Feb. 1, 2013, pp. 257-259, vol. 38, No. 3, Optical Society of America.
(Continued)

*Primary Examiner* — Tri T Ton
(74) *Attorney, Agent, or Firm* — Cantor Colburn LLP (57) ABSTRACT

The invention of the present application relates to a system for accurately measuring fine-dust precursors. Among apparatuses that measure concentrations of $NO_x$ and $SO_x$ which are precursors of fine dust by use of tunable diode laser absorption spectroscopy (TDLAS), an apparatus that can control a temperature of a measurement cell equipped with prism-type multi-passes by using thermoelectric elements without vibration is provided.

8 Claims, 10 Drawing Sheets

(51) Int. Cl.
*G01N 21/3504* (2014.01)
*G01N 33/00* (2006.01)

(52) U.S. Cl.
CPC ..... *G01N 21/3504* (2013.01); *G01N 33/0037* (2013.01); *G01N 33/0042* (2013.01)

(58) Field of Classification Search
CPC ...... G01N 21/03; G01N 21/031; G01N 33/00; G01N 2021/399
USPC ................ 356/432–444, 213–236, 335–343
See application file for complete search history.

(56) References Cited

U.S. PATENT DOCUMENTS

| | | | |
|---|---|---|---|
| 6,819,429 B2 * | 11/2004 | He | G02B 5/3025 356/454 |
| 7,116,848 B2 | 10/2006 | He et al. | |
| 2003/0174323 A1 | 9/2003 | Wagner et al. | |
| 2005/0094934 A1 | 5/2005 | He et al. | |
| 2014/0356985 A1 | 12/2014 | Ricci et al. | |
| 2016/0069797 A1 * | 3/2016 | Chanda | G01N 21/31 356/437 |
| 2018/0011003 A1 | 1/2018 | Baum et al. | |

FOREIGN PATENT DOCUMENTS

| | | |
|---|---|---|
| JP | 200733460 A | 2/2007 |
| JP | 2015135251 A | 7/2015 |
| JP | 2015155848 A | 8/2015 |
| KR | 20020027662 A | 4/2002 |
| KR | 1020040064506 A | 7/2004 |
| KR | 100481433 B1 | 4/2005 |
| KR | 1020060124111 A | 12/2006 |
| KR | 1020070075138 A | 7/2007 |
| KR | 100772201 B1 | 11/2007 |
| KR | 101159215 B1 | 6/2012 |
| KR | 1020160123762 A | 10/2016 |
| KR | 1020170026821 A | 3/2017 |
| KR | 101767177 B1 | 8/2017 |
| KR | 1020170103955 A | 9/2017 |

OTHER PUBLICATIONS

International Search Report dated Jan. 15, 2019 for PCT/KR2018/011802, citing the above reference(s).

* cited by examiner

FIG. 1

$$T_v = \left(\frac{I}{I_0}\right) = \exp(-k_v \cdot L)$$

$$k_v = S(T) \cdot P \cdot X_{abs} \cdot \emptyset_v$$

<Beer-Lambert Law>

$$X_{abs} = \frac{A}{S(T) \cdot P \cdot L}$$

$$T = \frac{\frac{hc}{k}(E_2'' - E_1'')}{\ln\frac{A_1}{A_2} + \ln\frac{S_2(T_0)}{S_1(T_0)} + \frac{hc}{k}\frac{(E_2'' - E_1'')}{T_0}}$$

Concentration Equation  Temperature Equation

OUTDOOR MULTI-PASS CELL FOR TDLAS

TECHNICAL FIELD

The invention of the present application relates to a system for accurately measuring fine-dust precursors, and more specifically, to an apparatus that measures a concentration of $NO_x$ and $SO_x$, which O are precursors of fine dust, by use of tunable diode laser absorption spectroscopy (TDLAS). In addition, the invention of the present application relates to an apparatus that is capable of controlling a temperature of a measurement cell without vibration so as to accurately measure fine-dust precursors outdoors at all times.

BACKGROUND ART

Fine dust and ultrafine particles mean particulate matters having a particle size of 2.5 μm and 1.0 μm, respectively, based on standards of WHO and are defined to have a particle size of 10 μm and 2.5 μm, respectively, in Republic of Korea.

Currently, one of main causes of the fine dust in Republic of Korea can comprise combustion in thermal power plants, and fine dust from the combustion in the thermal power plants is found to be 20 to 30% of fine dust production in Republic of Korea.

Compared to the amount of fine dust generated as solid fine dust from a generation source, such as carbon, soot, minerals, or the like, a larger amount of fine dust is generated through a chemical reaction of gaseous matter from a generation source with other matters in the air. Hence, in order to estimate or forecast a generation amount of fine dust, it is necessary to provide a highly accurate measurement system of $NO_x$ and $SO_x$ as main gases which are converted into secondary fine dust.

When concentrations of various gases such as $CO$, $CO_2$, $NO_x$ and $SO_x$, which are main causes of air pollution, are measured, a measurement method using a laser that can perform real-time measurement without sampling a measuring-target gas significantly holds the limelight. Gases which influence an air environment absorbs mainly infrared ray. The infrared ray is divided into a near-infrared ray (0.8 μm to 1.5 μm), a mid-infrared ray (1.5 μm to 5.6 μm), and a far-infrared ray (5.6 μm to 1,000 μm). A molecule vibrating mode or a molecule rotating mode is intensively activated by absorption of the mid-infrared ray. Thus the mid-infrared ray is applied to a direct absorption spectroscopy (DAS) measurement technique using molecular absorption of light, so as to achieve a highly effective method for measuring a concentration or temperature of a measuring-target gas.

Tunable diode laser absorption spectroscopy (hereinafter, referred to as 'TDLAS') is a method in which a tunable laser is used as a light source, and a concentration and a temperature are obtained by comparing ratios between an initial laser intensity ($I_0$) before transmission through a measurement region and a laser intensity (I) after the transmission through the measurement region where absorption occurs. This is performed based on the Beer-Lambert law.

Figure 1:
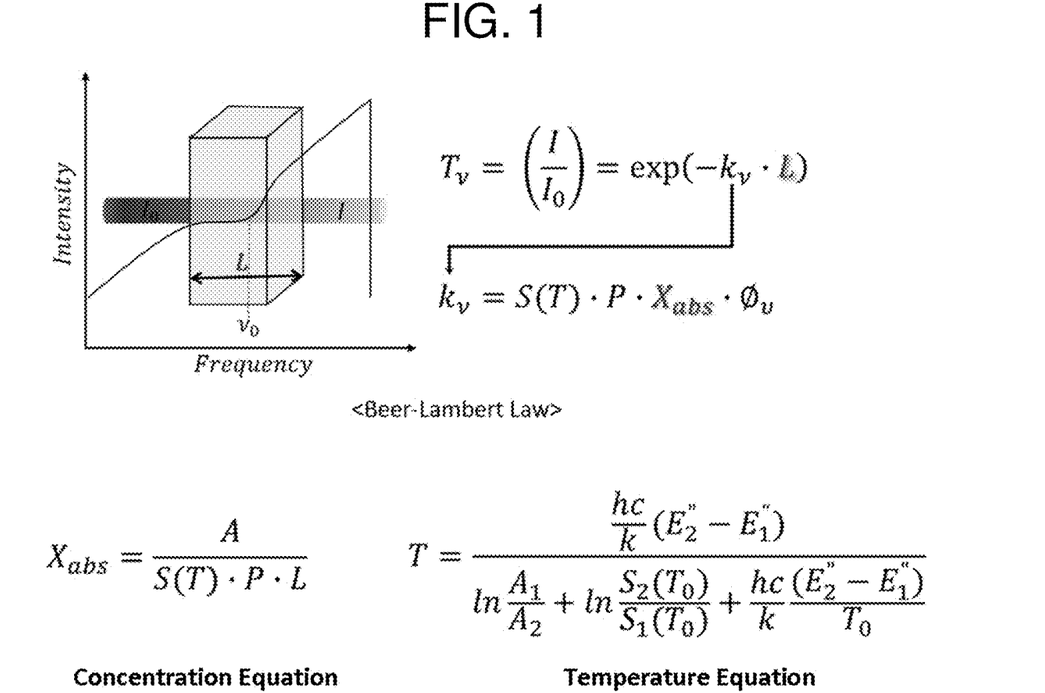
FIG. 1 shows calculation equations in accordance with the Beer-Lambert law in a tunable diode laser absorption spectroscopy (hereinafter, referred to as 'TDLAS').

As can be known from equations in FIG. 1, an absorption amount is proportional to an optical path length (L). If concentrations of measurement gases are very minute where fine-dust precursors to be detected, main variable for improvement of measurement is a measurement length L and a temperature T. When the fine-dust precursors are continuously measured outdoors in real time, an sampling cell for measurement is fixed, and thus the measurement length L does not change, but the temperature T continuously changes depending on seasons, day and night, or the like. Hence, constant and accurate temperature control is necessary to measure the fine-dust precursors having a low concentration by the TDLAS. On the other hand, the TDLAS itself is very accurate optical measurement equipment and, thus, is very vulnerable to external vibration. For this reason, when a conventional cooling system using a compressor is used, vibration generated therefrom is a significant restriction on use of the TDLAS. Even when the cooling system is installed at a long distance, vibration of a pump for transmitting a heating medium also disturbs accurate measurement of the TDLAS.

In this respect, it is highly necessary to develop an accurate TDLAS system equipped with a temperature control system suitable for an optical apparatus in an external environment, by which it is possible to accurately measure $NO_x$ and $SO_x$, which are major precursors that are to be converted into fine dust, in real time.

Patent Literature 1 relates to a pipe cooler and a small temperature regulator using the pipe cooler in a semiconductor-related manufacturing apparatus. A thermoelectric element is fixed closely to a surface of a heat exchange block with high heat capacity which exchanges heat with an end portion of a heat pipe, and heat transfer means is provided at side of the thermoelectric element, the side being opposite to the heat exchange block. The heat pipe has at least one heat-transfer extension portion projecting from the heat exchange block. Patent Literature 1 relates to a device that regulates a temperature of a heating medium around the heat exchange block and the heat-transfer extension portion of the heat pipe, by operation control of the thermoelectric element.

Patent Literature 2 relates to a substrate processing apparatus and a method for treating a substrate. The substrate processing apparatus comprises: a process chamber; a container that is positioned inside the process chamber and has a treatment space; a support unit that is positioned in the treatment space to support the substrate; a liquid supply unit that supplies a treatment liquid to the substrate placed on the support unit; and a temperature regulating unit that regulates a temperature of the treatment liquid which is to be supplied to the substrate. The temperature regulating unit provides a fluid by which heat is exchanged around the treatment liquid to maintain the temperature of the treatment liquid at a preset temperature and regulates the temperature of the treatment liquid by heating or cooling the treatment liquid before the treatment liquid is supplied to the substrate. In Patent Literature 2, a thermoelectric element is used as a device that regulates a temperature in semiconductor-related substrate treatment.

Patent Literature 3 relates to a temperature controlling assembly used when a substrate is treated in a vacuum chamber of a semiconductor treating apparatus. As already known, in order to control a temperature in a semiconductor manufacturing process, a thermoelectric element and a remote compression cooling system are used.

Patent Literature 4 relates to plasma processing equipment that comprises a process chamber in which plasma is formed, a chamber lid which is disposed on the process chamber, a chuck which is provided inside the process chamber and on which a wafer is seated, a pipe channel which is connected to the chamber lid, and a temperature control unit which is connected to the chamber lid through the pipe channel and enables a fluid having a constant temperature to circulate. In Patent Literature 4, it is described that a thermoelectric element is used to constantly maintain a temperature of the chamber lid.

Patent Literature 9 describes information on various multi-pass cells comprising a prism or the like as an optical spectrum analyzer. However, such an apparatus is not provided with consideration for an outside temperature, particularly, a temperature change between summer and winter. A highly accurate optical apparatus is characterized in that a reflection condition of a laser changes due to a temperature change, and thus it is not possible to obtain a desired result; however, regarding this, there is no description in Patent Literature 9.

Non Patent Literature 1 relates to a tube-type metal multipass optical cell for laser spectroscopy. A tube-shaped multipass optical cell was first developed in 1994 and has been used to measure matter having a low concentration mainly indoors. The multipass cell is applied by using a single cylinder-shaped mirror or disposing multiple flat mirrors in a circle. Irradiation with a laser beam is performed into an inside of the cell at a constant angle at which the laser beam is displaced from a center of a circle. The irradiated laser beam forms a star-like pattern inside the cell and, then, is emitted to an outside of the cell. The cell is suitable for measuring a concentration of a gas having a low concentration in a small volume.

Figure 4:
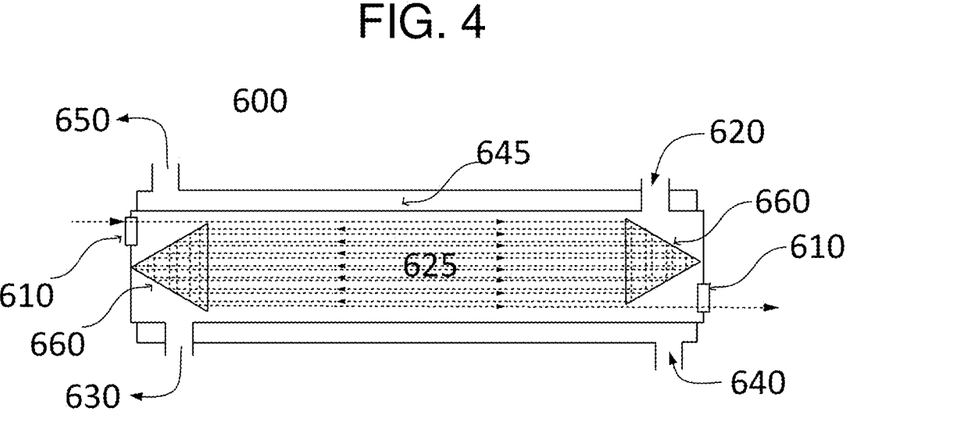
FIG. 4 is a schematic diagram of a measurement cell comprising a multi-passing prism according to the invention of the present application.

In Non Patent Literature 1, copper having a cylindrical shape is used to replace conventional mirror. An inside thereof is subjected to surface treatment through diamond processing and is plated with gold for additional reflection. An incident angle and a light-source distance of the tube-shaped multipass cell is disclosed in Non Patent Literature 1, and thus the detailed description thereof is omitted. FIG. 4 illustrates an inner heating-medium circulating channel according to the present application and a type of reflection pattern when the tube-shaped cell is irradiated with the laser.

Figure 3:
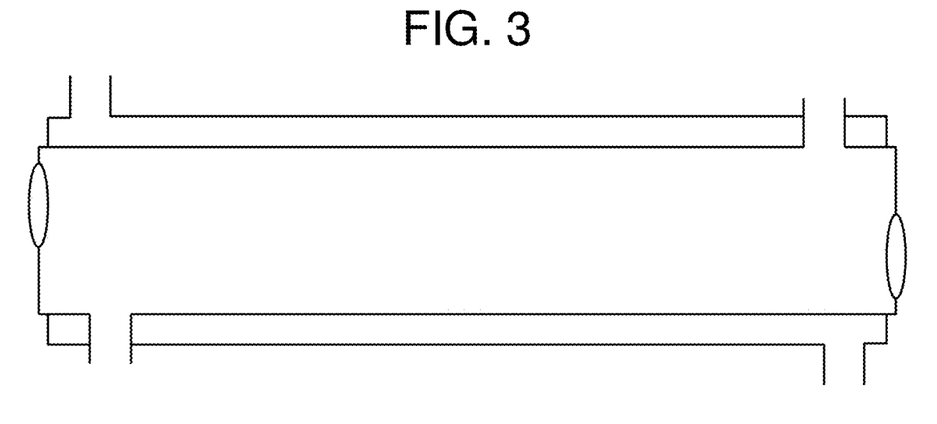
FIG. 3 is a schematic diagram of a measurement cell in the related art.

The metal cell has an advantage of being robust against physical stress. The metal cell is also more advantageous in temperature change than a conventional glass material (refer to FIG. 3). Temperature control is most important in order to measure fine-dust precursors outdoors. In particular, when a cell is made of copper for physical strength, the cell can be deformed due to a temperature change between summer and winter, and thus it is not possible to measure correctly.

In general, accurate optical equipment is rarely used outdoors. In addition, it is rarer to find outdoor optical apparatus equipped with a system that controls a temperature without vibration. An example of equipment that is capable of performing cooling and heating without vibration can comprise a thermoelectric element. However as described above, thermoelectric element currently used is very restrictively configured, also it is found that optical measurement equipment to which the TDLAS described in the present application is applied outdoors is not used.

CITATION LIST

Patent Literature

[Patent Literature 1]
  Japanese Unexamined Patent Publication No. 2001-133105 (May 18, 2001)
[Patent Literature 2]
  Korean Unexamined Patent Publication No. 10-2017-0026821 (Mar. 9, 2017)
[Patent Literature 3]
  U.S. Published Patent Application No. 2014-0356985 (Dec. 4, 2014)

[Patent Literature 4]
  Korean Unexamined Patent Publication No. 10-2007-0075138 (Jul. 18, 2007)
[Patent Literature 5]
  Korean Patent No. 10-0481433 (Mar. 28, 2005)
[Patent Literature 6]
  Korean Unexamined Patent Publication No. 10-2006-0124111 (Dec. 5, 2006)
[Patent Literature 7]
  Korean Unexamined Patent Publication No. 10-2004-0064506 (Jul. 19, 2004)
[Patent Literature 8]
  Korean Patent No. 10-0772201 (Nov. 1, 2007)
[Patent Literature 9]
  U.S. Pat. No. 7,116,848 (Oct. 3, 2006)
[Non Patent Literature 1]
  Optics letters, Feb. 1, 2013, Vol. 38, No. 3, pp 257

SUMMARY OF INVENTION

Technical Problem

The invention of the present application is made to solve such problems in the related art, and an object thereof is to provide an apparatus that is capable of controlling, without vibration, a temperature of a tunable diode laser absorption spectroscopy (TDLAS) device comprising a cell equipped with prism-shaped or tube-shaped multi-pass such that it is possible to accurately measure concentrations of $NO_x$ and $SO_x$, which are precursors of fine dust, outdoors by use of TDLAS.

Solution to Problem

According to a first aspect of the invention of the present application to solve the problems, there is provided an accurate concentration measuring apparatus of fine-dust precursors comprising: a laser unit which performs irradiation with a laser beam; a measurement cell in which a gas for measurement is captured and which has a multi-passing prism that the laser beam penetrates; a light detector to which laser beams emitted through the measurement cell are collected; a processing unit which performs analysis the measurement result by the laser beams; and a jacket-shaped heat exchanging unit which surrounds a periphery of the measurement cell and through which a heating medium having a constant temperature flows.

The measurement cell has a configuration in which two prisms are symmetrically disposed to finely displaced each other, and the laser beam travels into the measurement cell and travels out of the measurement cell after making multi-passes through total reflection of the prisms.

According to a second aspect of the invention of the present application, there is provided an accurate concentration measuring apparatus of fine-dust precursors comprising: a laser unit which performs irradiation with a laser beam; a measurement cell in which a gas for measurement is captured and which the laser beam penetrates; a light detector to which laser beams emitted through the measurement cell are collected; and a processing unit which performs analysis the measurement result by the laser beams. The measurement cell is a tube-shaped cell manufactured of metal, has one hole which enables the laser beam to travel in and out, the one hole being provided in a side surface of a tube, has an outlet which enables the gas for measurement to flow in or out, the outlet being provided at an upper surface or a lower surface of the tube, and has a passage through which a countercurrent heating medium can flow along an outer surface of the tube, and the laser beam is reflected multiple times in the tube.

The metal is coatable or plateable with any one of gold, silver, and chromium. A portion of the measurement cell, from which the laser beam is reflected, is coated or plated with any one of gold, silver, and chromium.

The laser unit may be a tunable diode laser or a distributed feedback laser.

The heating medium is at least one of water, a gas, oil, and an inorganic heat-transfer medium. The heating medium is heated or cooled by a temperature control module comprising thermoelectric elements. Specifically, the temperature control module comprises a thermoelectric-element module that has multiple thermoelectric elements and a printed circuit board at which a conductive pattern is formed to electrically connect the multiple thermoelectric elements, and an upper heat exchanger and a lower heat exchanger that are in contact with upper surfaces and lower surface of the multiple thermoelectric elements, respectively. On the other hand, the fine-dust precursors are $NO_x$ and $SO_x$.

Temperatures of the thermoelectric elements may be regulated in a state where the thermoelectric elements are directly attached to the measurement cell without the heat exchanging unit.

Flow of the heating medium may be controlled by a pump that does not generate vibration, represented by a peristaltic pump. It is desirable for the pump to be disposed separately from a device such as a table at which optical measurement is dispatched.

According to a third aspect of the invention of the present application, there is provided a method for controlling a temperature of a measurement cell of an accurate concentration measuring apparatus of fine-dust precursors using an optical system that comprises: a laser unit which performs irradiation with a laser beam; a measurement cell in which a gas for measurement is captured and which has a multi-passing prism that the laser beam penetrates; a light detector to which laser beams emitted through the measurement cell are collected; and a processing unit which performs analysis the measurement result by the laser beams. A jacket-shaped heat exchanging unit, through which a heating medium having a constant temperature flows, surrounds a periphery of the measurement cell, and a temperature control module having thermoelectric elements heats or cools the heating medium, or a temperature of the thermoelectric elements is controlled in a state where the thermoelectric elements are directly attached to the measurement cell.

Advantageous Effects of Invention

As described above, a system for measuring fine-dust precursors according to the invention of the present application has a merit of being capable of accurately measuring concentrations of $NO_x$ and $SO_x$, which are the fine-dust precursors, even at an outdoor place at all times. In particular, it is possible to constantly maintain a temperature of a measurement cell without vibration regardless of day and night, and thus the system has a merit of being capable of measuring concentrations of $NO_x$ and $SO_x$ having low concentrations without an error.

DESCRIPTION OF EMBODIMENTS

Hereinafter, the description is provided with reference to the drawings according to embodiments of the invention of the present invention; however, the description is provided for better understanding of the invention of the present application, and the scope of the invention is not limited thereto.

Figure 2:
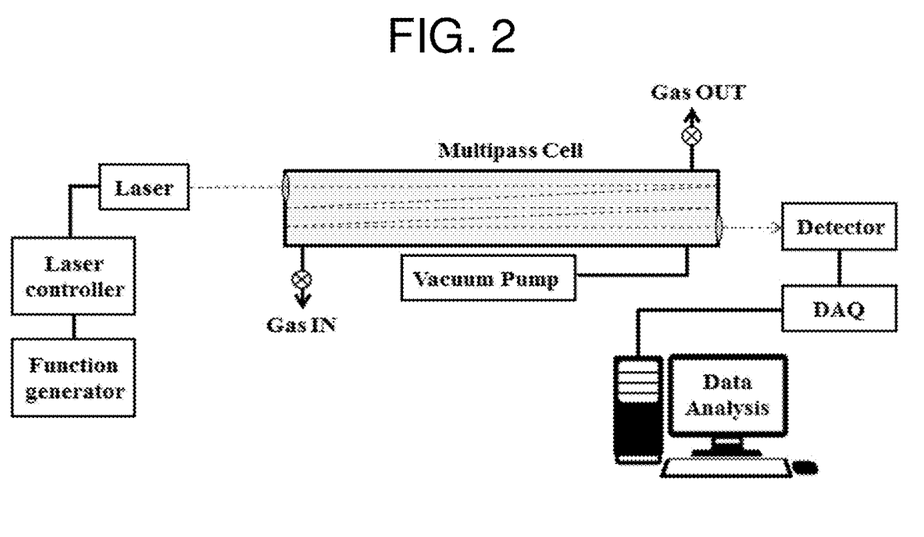
FIG. 2 is a schematic diagram of a TDLAS measurement apparatus according to an embodiment of the invention of the present application.

TDLAS is a measurement system using a tunable diode laser and is recently attracting much attention among real-time measurement systems. FIG. 2 shows a representative TDLAS-related configuration, and technical details of the TDLAS itself are described in Patent Literatures 5, 6, and 7. Hence, the detailed description thereof is omitted.

An apparatus having a measurement cell according to FIG. 4 is configured of an accurate concentration measuring apparatus for fine-dust precursor comprising: a laser unit which performs irradiation with a laser beam; a measurement cell in which a gas for measurement is captured and which has a multi-passing prism that the laser beam penetrates; a light detector to which laser beams emitted through the measurement cell are collected; a processing unit which performs analysis the measurement result by the laser beams; and a jacket-shaped heat exchanging unit which surrounds a periphery of the measurement cell and through which a heating medium having a constant temperature flows.

The measurement cell has a configuration in which two prisms are symmetrically disposed to finely displaced each other, and the laser beam travels into the measurement cell and travels out of the measurement cell after making multi-passes through total reflection of the prisms. A common prism can be used as the prisms. In particular, as the prisms at a symmetrical position disposed to finely displaced each other, an internal total reflection pass elongates such that it is advantageous for measuring fine-dust precursors having a low concentration. On the other hand, although not shown directly on the drawings, there is a method for constantly maintaining a temperature of the prism by controlling a temperature inside the measurement cell, and it is possible to employ a method for controlling a temperature by circulating a heating medium directly around the prism.

The laser unit can be a tunable diode laser or a distributed feedback laser. In general, the laser has a fixed wavelength; however, the wavelength can be modulated using a diode laser, and it is possible to perform modulation by a function generator.

In order to accurately measure a concentration of a precursor, it is important to constantly maintain the temperature of the measurement cell. FIG. 4 shows a prism measurement cell 600 according to the invention of the present application, and the prism measurement cell 600 is equipped with a lens 610 through which the laser beam travels in and a lens 610 through which the laser beam travels out after inner reflection at either side of the measurement cell 600. Measurement-gas inlet and outlet 620 and 630, which enable a gas for measurement to flow in a measurement-gas chamber 625 and then to be discharged outside, are provided at one end and the other end of the measurement cell 600. A jacket-shaped heat exchanging unit is provided outside such that a temperature of the measurement-gas chamber 625 can be maintained. Heating-medium inlet and outlet 640 and 650, which enable a heating medium, which is mainly water, to flow in and out, are provided at one end and the other end of the heat exchanging unit such that the heating medium having a desired temperature can be continuously circulated.

Two prisms 660 are symmetrically disposed to finely displaced each other so as to perform total reflection inside the measurement cell 600.

Figure 5:
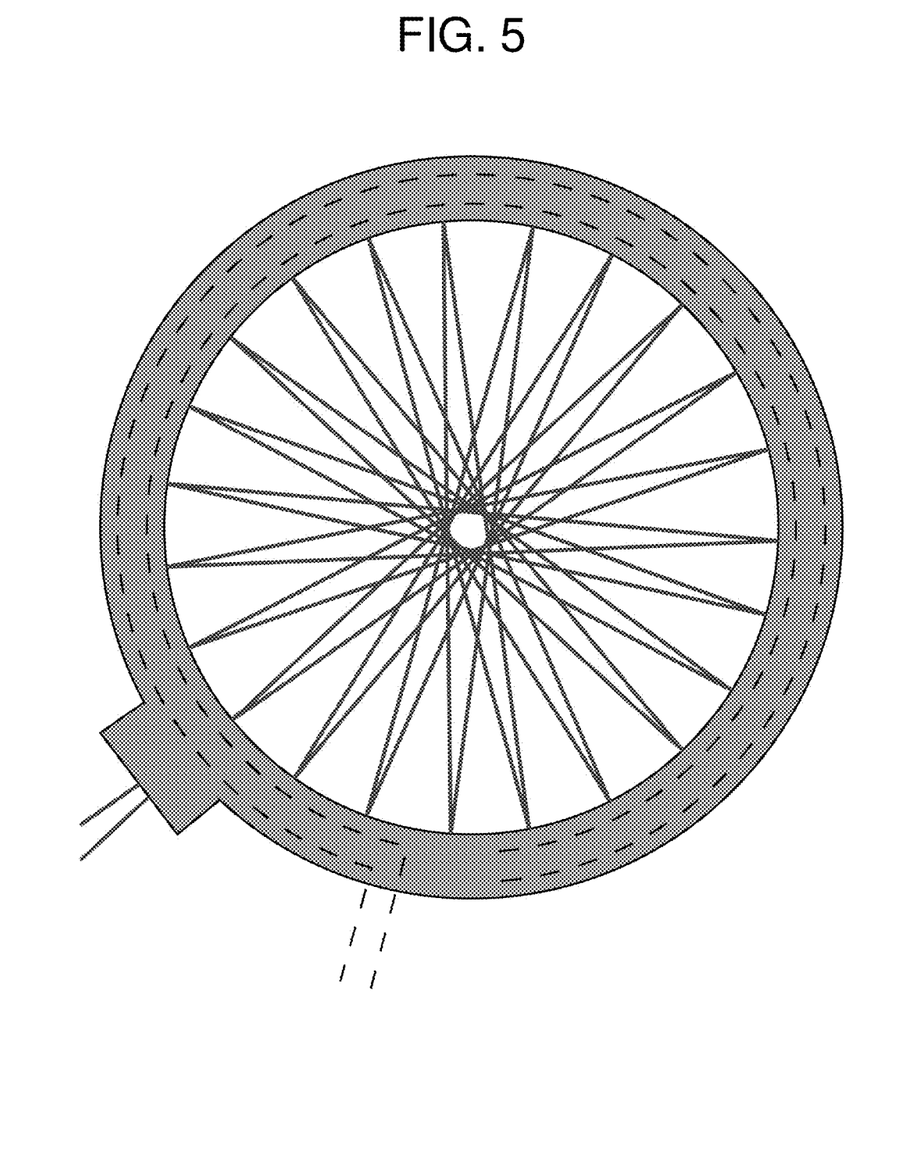
FIG. 5 is a diagram optically showing a tube-shaped cell according to the invention of the present application.

An apparatus having a tube-shaped cell in FIG. 5 is configured of an accurate concentration measuring apparatus for fine-dust precursor comprising: a laser unit which performs irradiation with a laser beam; a measurement cell in which a gas for measurement is captured and which the laser beam penetrates; a light detector to which laser beams emitted through the measurement cell are collected; and a processing unit which performs analysis the measurement result by the laser beams. The measurement cell is a tube-shaped cell manufactured of copper (metal), has one hole which enables the laser beam to travel in and out of the tube, the one hole being provided in a side surface of the tube, has an outlet which enables the gas for measurement to flow in or out, the outlet being provided at an upper surface or a lower surface of the tube, and has a passage through which a countercurrent heating medium can flow along an outer surface of the tube, and the laser beam is reflected multiple times in the tube.

The laser unit can be a tunable diode laser or a distributed feedback laser. In general, the laser has a fixed wavelength; however, the wavelength can be modulated using a diode laser, and it is possible to perform modulation by a function generator.

In order to accurately measure the concentration of the precursor, it is important to constantly maintain the temperature of the measurement cell. In particular, since the cell according to the invention of the present application is manufactured of copper (metal), and the cell can be deformed due to a temperature change, so it is most important to maintain a constant temperature. FIGS. 5 to 9 show a tube-shaped measurement cell 400 according to another embodiment of the invention of the present application, and the tube-shaped measurement cell 400 has a laser inlet/outlet 410, which enables the laser to travel in and out, at one side of the cell. Measurement-gas inlet and outlet 420 and 430, which enable a gas for measurement to flow in a measurement-gas chamber 425 and then to be discharged outside, are provided at one end and the other end of the measurement cell 400. On an inner cross section of the cell, a heating-medium moving section 445 is provided to constantly maintain a temperature of the measurement-gas chamber 425. Heating-medium inlet and outlet 440 and 450, which enable a heating medium, that is, mainly water, to flow in and out, are provided at a side surface of the cell such that the heating medium having a desired temperature can be continuously circulated.

Figure 6:
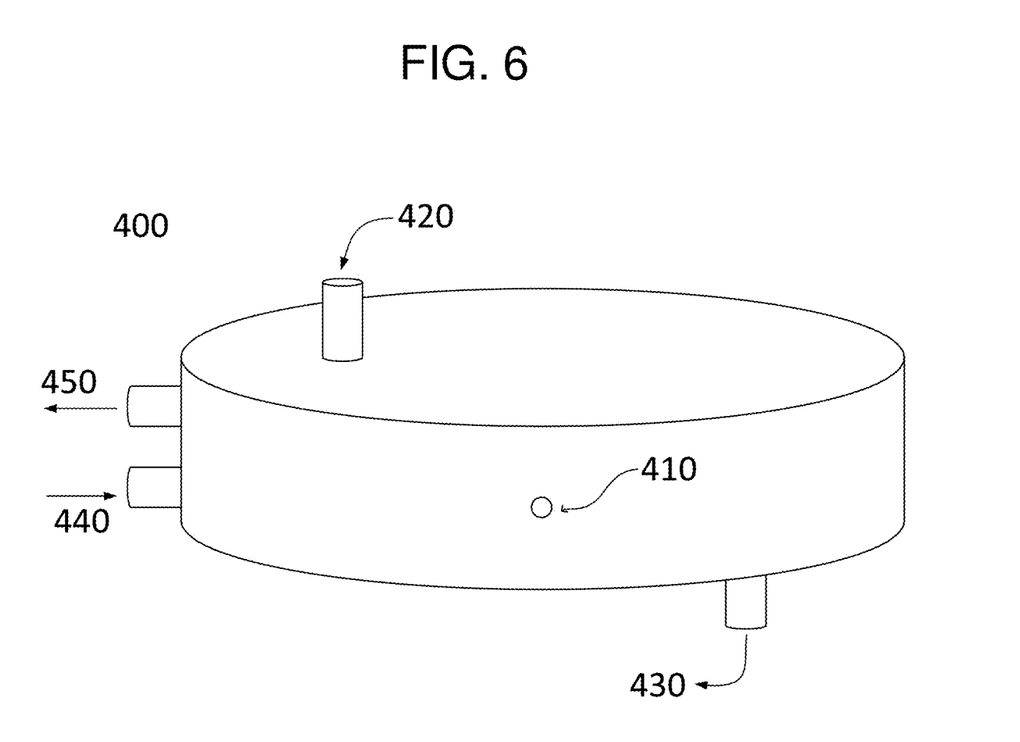
FIGS. 6 to 9 are schematic diagrams of the tube-shaped cell according to the invention of the present application.
Figure 7:
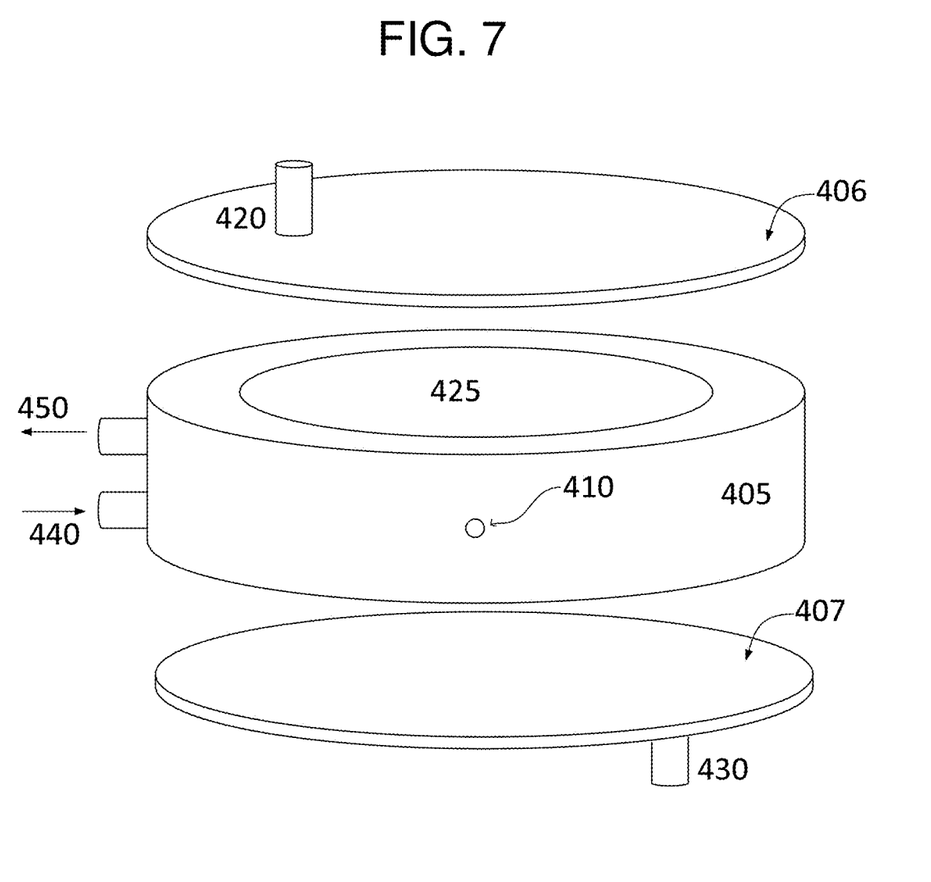

FIG. 7 shows a shape of the cell from which an upper lid 406 and a lower lid 407 are separated, and FIG. 6 shows a shape of the cell to which the upper and lower lids are joined.

Figure 8:
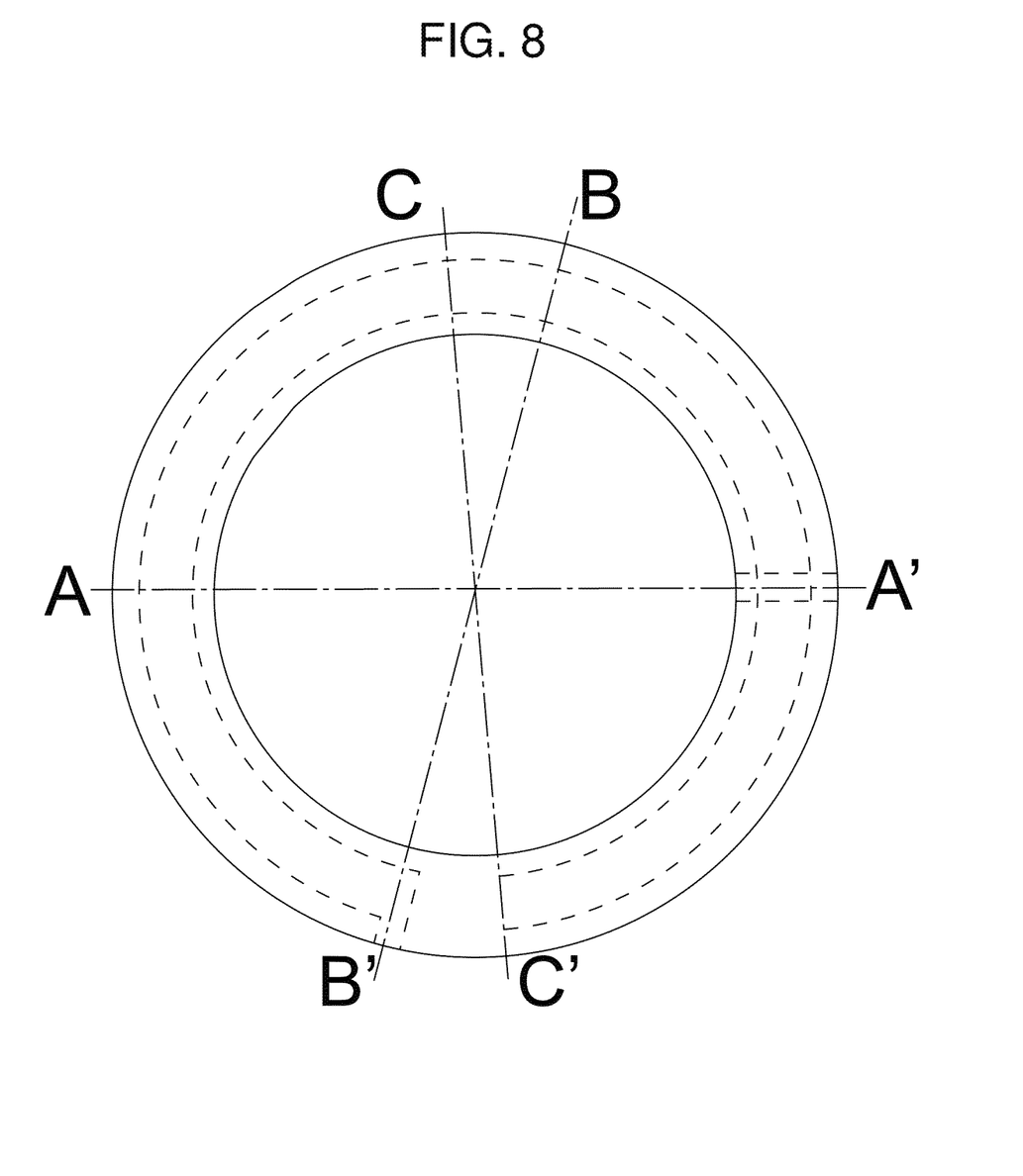
Figure 9:
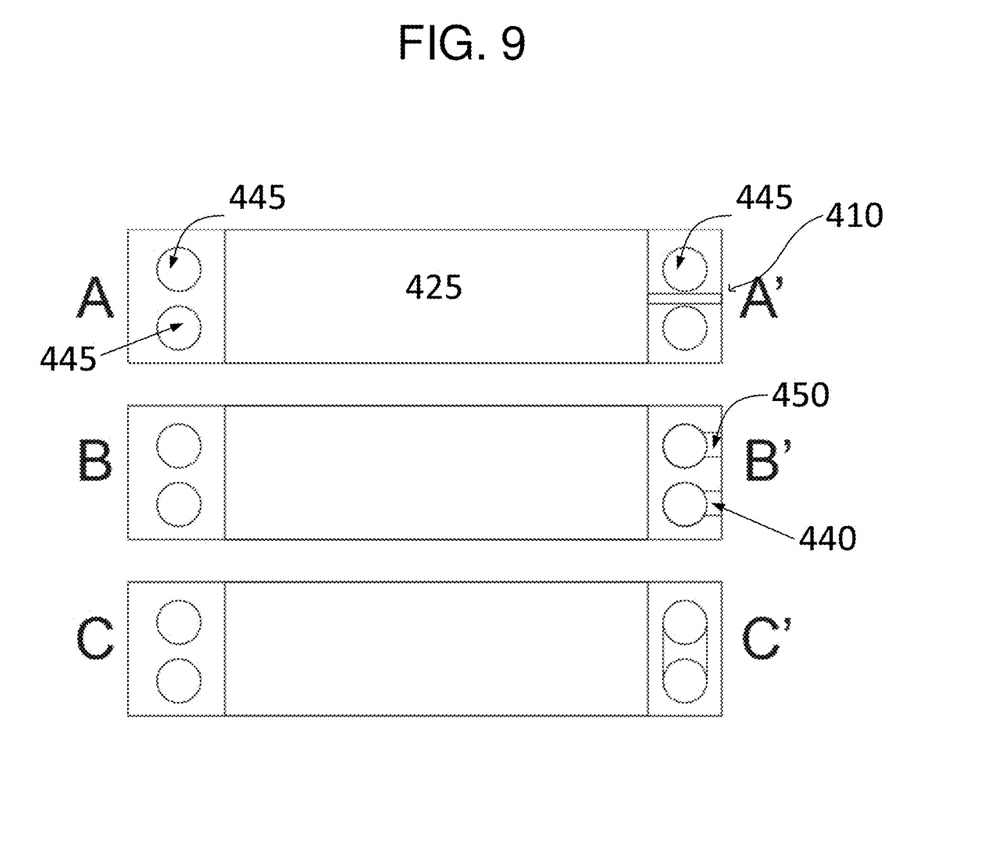

FIG. 8 shows a shape of a main cell body 405 from above, in which the main cell body 405 has the heating-medium moving section 445 through which the heating medium is circulated such that a temperature of the measurement-gas chamber 425 is constantly maintained. FIG. shows cross sections taken along AA', BB', and CC', respectively. Donut-shaped empty spaces at upper and lower sides with reference to the laser inlet/outlet 410 are the heating-medium moving sections 445.

The heating medium flows in through one of the heating-medium inlet and outlet 440 and 450, circulates through the substantially entire heating-medium moving section 445 along a tube shape and flows toward the upper or lower heating-medium moving section through a point viewed on a CC' cross section at which the upper and lower donut-shaped heating-medium moving sections 445 are connected to each other and circulates along a substantially entire tube shape again, and then is discharged through the heating-medium inlet and outlet 440 and 450. A flowing-in heating medium and a flowing-out heating medium are always counter-currently disposed, and thus the entire temperature of the cell is uniformly maintained due to an average temperature of the mediums. It is desirable to form double inner tubes at an outer surface of the tube-shaped measurement cell 400 through a method of forming groove inward from outside, connecting necessary portions, and then covering the groove.

Figure 10:
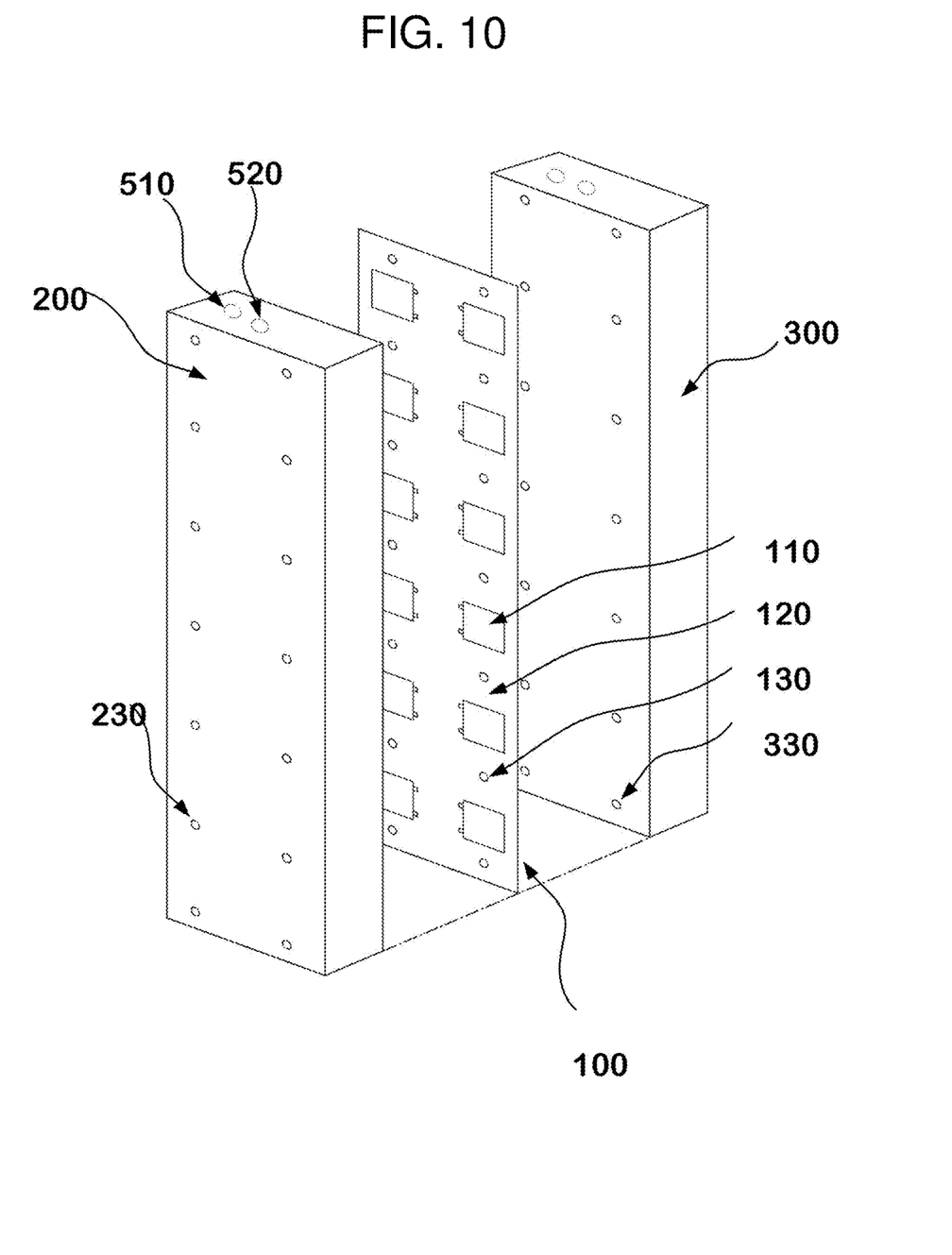
FIG. 10 is a schematic view of a temperature control module according to an embodiment of the invention of the present application.

A temperature control module comprising thermoelectric elements is an apparatus that is capable of controlling, without vibration, the temperature of the heating medium used in the prism measurement cell 600 and the tube-shaped measurement cell 400. FIG. 10 shows the temperature control module according to an embodiment of the invention of the present application. A thermoelectric element 110 is configured to have a pair of ceramic panels which is separated by a constant distance, a plurality of N-type and P-type thermoelectric semiconductors which are provided between the pair of ceramic panels and are arranged in a predetermined pattern, a conductive electrode that electrically connects the plurality of N-type and p-type thermoelectric semiconductors in series, and electrode terminals that are joined to respective terminals of the conductive electrode and is used for applying electric power to the plurality of N-type and P-type thermoelectric semiconductors.

A space formed between the pair of ceramic panels is filled with a silicon layer such that configurational elements are prevented from being separated from each other due to an external force and moisture is prevented from flowing into an inside thereof.

Specifically, the temperature control module comprises a thermoelectric-element module 100 that has multiple thermoelectric elements 110 and a printed circuit board 120 at which a conductive pattern is formed to electrically connect the multiple thermoelectric elements 110, and an upper heat exchanger 200 and a lower heat exchanger 300 that are in contact with upper surfaces and lower surfaces of the multiple thermoelectric elements 110, respectively. The temperature control module has a fastening member (not shown) which fixes the thermoelectric-element module 100, the upper heat exchanger 200, and the lower heat exchanger 300. A fastening member 30 is mounted using mounting holes 130, 230 and 330.

The upper or lower heat exchanger 200 or 300 has a heat-exchange fluid inlet 510 formed at an cross-section of one end thereof and a heat-exchange fluid outlet 520 formed at the same cross-section as that of the heat-exchange fluid inlet, and an inner circulation section that starts from the heat-exchange fluid inlet, circulates through the inside of the heat exchanger, and is connected to the heat-exchange fluid outlet. In the inner circulation section, an inflow fluid and an outflow fluid are always counter-currently disposed as a pair. Technical details of the temperature control module are described in Patent Literature 8, and thus the detailed description thereof is omitted.

The flow of the heating medium can be controlled by a pump that does not generate vibration, represented by a peristaltic pump. It is desirable for the pump to be disposed separately from a device such as a table at which optical measurement is dispatched.

As described above, the system for measuring the fine-dust precursors according to the invention of the present application has a merit of being capable of accurately measuring concentrations of $NO_x$ and $SO_x$, which are the fine-dust precursors, even at an outdoor place at all times. In particular, it is possible to constantly maintain the temperature of the measurement cell without vibration regardless of seasons and day and night, and thus the system has a merit of being capable of measuring concentrations of $NO_x$ and $SO_x$, having low concentrations without an error.

It is possible for a person of ordinary knowledge in the technical field, to which the invention of the present application belongs, to perform various applications and modifications based on the above descriptions within the scope of the invention of the present application.

REFERENCE SIGNS LIST

100 THERMOELECTRIC ELEMENT MODULE
110 THERMOELECTRIC ELEMENT
120 PRINTED CIRCUIT BOARD
130, 230, 330 MOUNTING HOLE
200, 300 HEAT EXCHANGER
400 MEASUREMENT CELL
405 MAIN CELL BODY
406, 407 UPPER LID AND LOWER LID
410 LASER INLET/OUTLET
420, 430 MEASUREMENT-GAS INLET AND OUTLET
425 MEASUREMENT-GAS CHAMBER
440, 450 HEATING-MEDIUM INLET AND OUTLET
445 HEATING-MEDIUM MOVING SECTION
600 PRISM MEASUREMENT CELL
610 LENS
620, 630 MEASUREMENT-GAS INLET AND OUTLET
625 MEASUREMENT-GAS CHAMBER
640, 650 HEATING-MEDIUM INLET AND OUTLET
645 HEATING-MEDIUM MOVING SECTION
660 REFLECTING PRISM
510, 520 HEATING-MEDIUM INLET AND OUTLET

The invention claimed is:

1. An accurate concentration measuring apparatus of fine-dust precursors comprising:
a laser unit which performs irradiation with a laser beam;
a measurement cell in which a gas for measurement is captured and which has a prism that the laser beam penetrates;
a light detector to which laser beams emitted through the measurement cell are collected;
a processor which performs analysis the measurement result by the laser beams; and
a heater which surrounds a periphery of the measurement cell and through which a heating medium having a constant temperature flows,
wherein the heating medium is at least one of water, a gas, oil, and an inorganic heat-transfer medium, and
wherein the heating medium is heated or cooled by a temperature control module comprising thermoelectric elements,
wherein the temperature control module comprises
a thermoelectric-element module that has multiple thermoelectric elements and a printed circuit board at which a conductive pattern is formed to electrically connect the multiple thermoelectric elements, and
an upper heat exchanger and a lower heat exchanger that are in contact with upper surfaces and lower surface of the multiple thermoelectric elements, respectively.

2. The accurate concentration measuring apparatus of fine-dust precursors according to claim 1,
wherein the measurement cell has a configuration in which two prisms are symmetrically disposed to finely displaced each other, and the laser beam travels into the measurement cell and travels out of the measurement cell after making multi-passes through total reflection of the prisms.

3. The accurate concentration measuring apparatus of fine-dust precursors according to claim 1,
wherein the laser unit is a tunable diode laser or a distributed feedback laser.

4. The accurate concentration measuring apparatus of fine-dust precursors according to claim 1,
wherein the thermoelectric elements are directly attached to the measurement cell directly without a heat exchanging unit.

5. The accurate concentration measuring apparatus of fine-dust precursors according to claim 1,
wherein the fine-dust precursors are $NO_x$ and $SO_x$.

6. The accurate concentration measuring apparatus of fine-dust precursors according to claim 1,
wherein the heating medium is caused to flow by a pump that does not generate vibration.

7. The accurate concentration measuring apparatus of fine-dust precursors according to claim 6,
wherein the pump is a peristaltic pump.

8. A method for controlling a temperature of the measurement cell of the accurate concentration measuring apparatus of fine-dust precursors according to claim 1 using an optical system that comprises:
the laser unit which performs irradiation with the laser beam;
the measurement cell in which the gas for measurement is captured and which the laser beam penetrates;
the light detector to which the laser beams emitted through the measurement cell are collected; and
the processor which performs analysis of the measurement result by the laser beams;
wherein the heater, through which the heating medium having the constant temperature flows, surrounds the periphery of the measurement cell, and the temperature control module having the thermoelectric elements heats or cools the heating medium, or
wherein a temperature of the thermoelectric elements is controlled in a state where the thermoelectric elements are directly attached to the measurement cell.

* * * * *